United States Patent [19]

Fukushima

[11] 4,330,892

[45] May 25, 1982

[54] MATTRESS AND BEDCLOTHES, OR PILLOW

[75] Inventor: Kyuji Fukushima, Seki, Japan

[73] Assignee: Kabushiki Kaisha Hatsuyume Wata Sohonpo, Tokyo, Japan

[21] Appl. No.: 208,016

[22] Filed: Nov. 18, 1980

[51] Int. Cl.³ .................. A47G 9/00; A47C 21/04
[52] U.S. Cl. ........................... 5/437; 5/421; 5/462; 5/490; 128/1.3
[58] Field of Search ............. 5/448, 434, 436, 421, 5/462, 485, 490, 437; 297/180; 128/1.3

[56] References Cited

U.S. PATENT DOCUMENTS

| | | | |
|---|---|---|---|
| 123,016 | 1/1872 | Harrington | 5/448 |
| 2,339,617 | 1/1944 | Clark | 5/448 |
| 2,368,930 | 2/1945 | Lenz | 5/448 |
| 3,162,868 | 12/1964 | Cramer | 5/490 |
| 3,269,621 | 8/1966 | Dishart | 5/462 |
| 4,143,435 | 3/1979 | Masuda | 5/481 |

FOREIGN PATENT DOCUMENTS

| | | | |
|---|---|---|---|
| 17534 | of 1887 | United Kingdom | 5/451 |
| 2025234 A | 1/1980 | United Kingdom | 5/448 |

*Primary Examiner*—Alexander Grosz
*Attorney, Agent, or Firm*—Bernard, Rothwell & Brown

[57] ABSTRACT

A mattress (futon or thick bedquilt) and bedclothes, or a pillow which comprises fillings, a plurality of permanent magnet pieces provided on a mounting means, and a covering cloth for covering the above-mentioned components. These magnet pieces generate lines of magnetic force and which are projected on a user's head or other portions of his body thereby to improve the user's health. On the other hand, these magnet pieces abut on the user's body through its covering cloth at the time of applying these mattress and bedclothes as well as pillow, thereby effecting functions of finger-pressure. Further since the pillow contains a heat-absorptive material such as adzuki beans as the fillings, such pillow functions to keep a user's head cool and his feet warm.

4 Claims, 3 Drawing Figures

MATTRESS AND BEDCLOTHES, OR PILLOW

BACKGROUND OF THE INVENTION

1. Field of the Invention

This invention relates to a mattress (futon or thick bedquilt) and bedclothes, or a pillow, and more particularly, to so-called healthy mattress and bedclothes, or a pillow the inside of which a plurality of small magnet pieces are arranged.

2. Prior Art of the Invention

In reference to a bracelet, necklace and the like, personal ornaments in which magnetism is utilized for promoting a user's health have heretofore been proposed.

Meanwhile blood flowing through blood vessel contains ion therein and flow of such ion may be assumed to be a kind of electric current. Thus, when magnetic field is applied to the blood vessel, a force acts on the inside thereof in accordance with Fleming's rule. Conversely it is said that when the magnetic field applied to the blood vessel is cut off, electric current flow through the blood vessel, whereby the flow of blood is influenced.

Among those which utilize the above principle, a permanent magnet having a surface magnetic flux density of about 500–800 gauss has particularly been employed for healthy personal ornaments. When lines of magnetic force from the magnet or magnets in personal ornaments utilizing magnetism therefrom are projected on a part of the user's body, a kind of electrically generates in the blood so that circulation of the blood becomes favorable. Furthermore blood is a good conductor of electricity as mentioned above and when weak electricity generates in the blood, molecules charged with the electricity circulate in the body, so that the human body is favorably affected.

On the other hand, when the human body becomes fatigued, metabolic decomposition product accumulates inside the blood vessel, or the body turns into the one of acidic constitution. In this situation, when red corpuscles in the blood of the above acidic constitution are affected by magnetic action, absorption of oxygen is improved, whereby the red corpuscles turn red. In addition calcium ions required for weak alkaline constitution which is one of conditions in healthy constitution increase and consequently, the human body is favorably influenced.

SUMMARY OF THE INVENTION

It is an object of the present invention to provide mattress and bedclothes, or a pillow by which a user's health can be promoted by means of magnetic action.

It is another object of the present invention to provide a mattress (or futon) on the upper surface of which a plurality of projections are formed and by which a user's health can be further improved by finger-pressure functions due to the projections so formed.

It is a further object of the present invention to provide a pillow which is filled with a heat-absorptive material such as adzuki beans and the like, so that a user can get a good sleep by such heat-absorptive material due to a so-called function to keep the head cool and the feet warm.

It is a still further object of the present invention to provide a futon stuffed with resilient fillings such as cotton wool and the like which can be re-willowed or regenerated.

The above and other objects and advantages of the present invention will be fully understood by reading the following description setting forth preferred embodiments of the present invention in connection with the accompanying drawing.

PREFERRED EMBODIMENTS OF THE INVENTION

Figure 1:
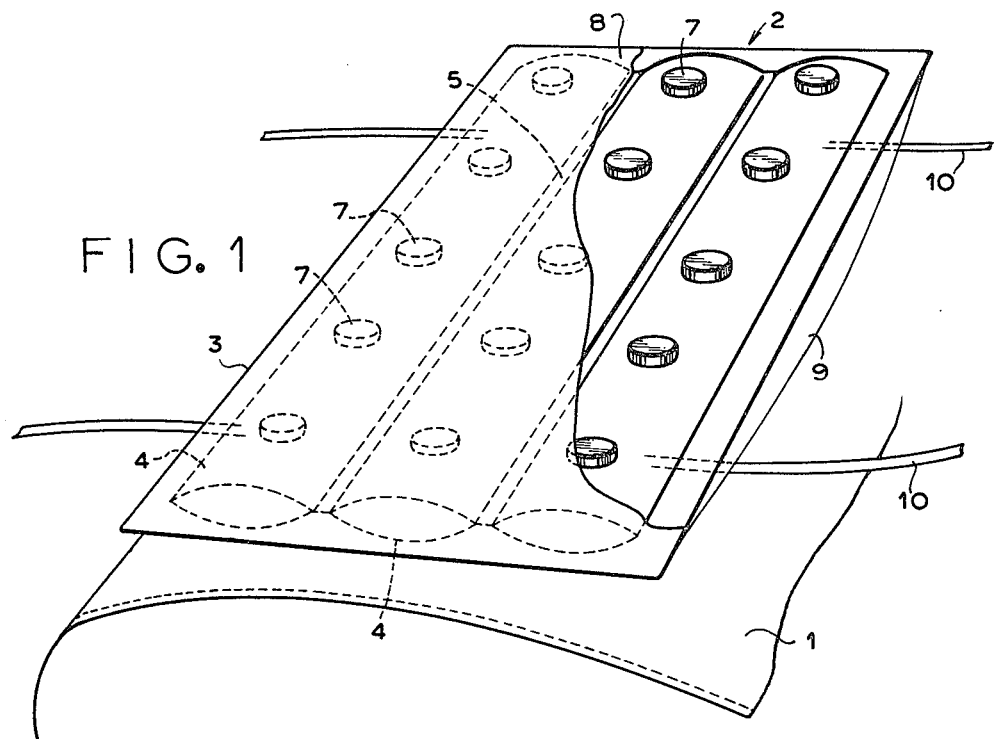
FIG. 1 is a perspective view showing a pillow in accordance with an embodiment of the present invention.
Figure 2:
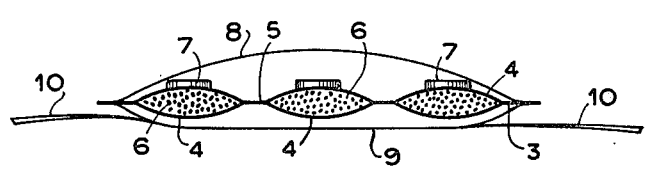
FIG. 2 is a sectional view, in elevation, showing a pillow pad employed in the pillow of FIG. 1.

A pillow according to one embodiment of the invention will be described hereinbelow by referring to FIGS. 1 and 2 in which the pillow consists of a pillow body 1 and a pillow pad 2 which is to be attached to the upper surface of the pillow body 1. A plurality of envelopes 4 being independently sealed from each other form a substratum 3 of the pillow pad 2. The respective envelopes 4 are arranged in parallel to each other with a suitable spacing 5 in order that the pillow pad 2 transforms easily, adjusting its shape by bending, and fits suitably the pillow body 1 dependent upon shapes, types and dimensions thereof to which the pillow pad 2 is attached. The envelope 4 is filled with adzuki beans 6 with a space by which the envelope 4 itself may easily transforms, by bending, in right and left as well as top and bottom directions, respectively. Since these adzuki beans are employed for effecting such advantage that unnecessary heat on the head of a user is absorbed to keep the head cool, a heat-absorptive material having a similar effect as mentioned above, for example, buckwheat chaffs, corns and the like may, of course, be utilized. On the upper surface of the envelope 4, i.e., the side on which a user's head abuts at the time of application of the pillow, a plurality of magnets 7 are fixedly arranged in its longitudinal direction. It is preferable to employ permanent magnet having a magnetic flux density of 500 gauss or more as the magnet 7. That is, when permanent magnet having a magnetic flux density of 500 gauss or more is applied to the human body, electric current generates in blood or human anatomy of the user by means of lines of magnetic force functions to effect ionization, and it results in the promotion of circulation of the blood, so that therapeutic effects upon various diseases due to troubles in respect of the blood can be achieved.

In the above embodiment, although the pillow pad in which the substratum 3 has three envelopes and they are arranged in parallel to the longitudinal direction of the pillow body 1, respectively, and five magnets 7 are provided on the upper surface of each envelope 4 is illustrated, it is, of course, possible to suitably increase and decrease, or modify the number of the magnets 7 and arrangement of the envelopes 4 with respect to the pillow body 1.

Since an upper cover 8 and lower cover 9 of the pillow pad 2 are, for example, sewn up together with the substratum 3 in margins of its three sides, they are stably and firmly secured to cover whole the substratum 3 and the magnets 7. Thus the pillow pad 2 is formed in such that the entire substratum 3 can be taken out from the side along which both margins of the upper and lower covers 8 and 9 are not sewn up together with the substratum, so that the whole substratum 3 can directly be exposed to the sun if desired.

In addition a pair of strings 10 for attaching the pillow pad 2 to the pillow body 1 are provided on the lower cover 9 abutting on the pillow. The string 10 has a sufficient length for positively attaching the pillow pad 2 to a pillow body of any shape, dimension and type.

Figure 3:
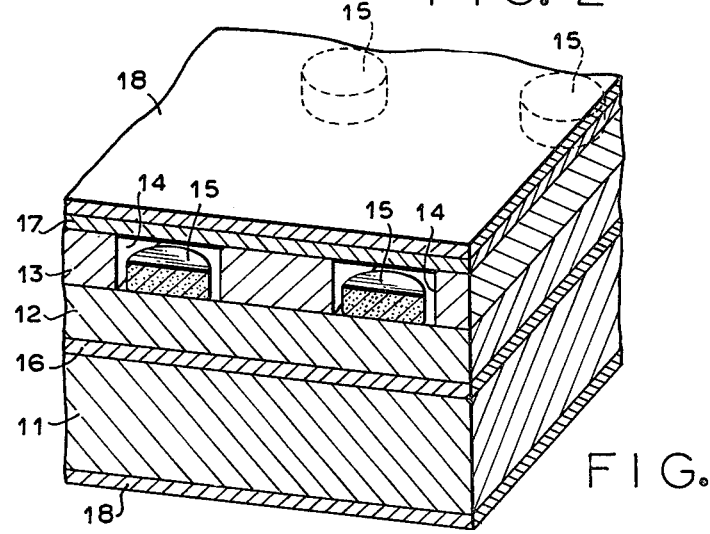
FIG. 3 is an explanatory view showing essential parts of a futon in accordance with another embodiment of the present invention.

FIG. 3 shows a part of futon according to another embodiment of the present invention. The futon comprises a principal constituent 11 such as mixed cotton fillings consisting of 60% cotton and 40% Tetron (trade name, manufactured by Toyo Rayon K.K. and Teikoku Jinken K.K.), a first felt mat 12 having 10 mm thickness which is placed on the principal constituent 11, and a second felt mat 13 which is a substantially same thickness as that of the first felt mat and is placed on the first felt mat 12. A number of holes 14, 14, . . . , preferably even-numbered holes are formed in the second felt mat 13. In these holes 14, 14, . . . , permanent magnet pieces 15, 15, . . . each being formed so as to have a thinner thickness than that of the second felt mat 13 are contained. In this embodiment, it is to be noted that a thickness (height) of the permanent magnet 15 is adjusted to be half the thickness of the second felt mat 13. Furthermore a cheesecloth 16 is placed between the principal constituent 11 and the first felt mat 12, and another cheesecloth 17 is placed on the surface of the second felt mat 13. The resulting piled materials consisting of the principal constituent 11, both the felt mats 12 and 13, and both the cheeseclothes 16 and 17 are covered by a covering cloth 18 together with permanent magnet pieces 15, 15, . . . to compose a futon.

The mattress, futon, bedclothes and pillow of the invention constructed as above stabilize user's nerves, particularly those of one who is in hypotension, neurosis, anaemia and insomnia by means of lines of magnetic force generated from magnets at the time of applying the mattress and bedclothes, or the like, thereby giving effectively a restful sleep to the user.

Furthermore the futon, mattress and bedclothes, and pillow according to the present invention have functions of finger-pressure, because the magnet pieces provided on these mattress and bedclothes and the like project through their covering clothes to contact with the user's body at the time of the application thereof.

Moreover the pillow according to the present invention suitably fits the user's head at all times irrespective of its shape, type and dimension, because the envelopes in the pillow pad are independently sealed from each other, so that they may easily be transformed in right and left as well as top and bottom directions, respectively. In addition since the envelope is filled with a heat-absorptive material, unnecessary heat on the user's head is absorbed thereby to keep the head cool, so that a comfortable sleep of the user is promoted due to a special efficacy of keeping the head cool and the feet warm.

Still further, according to the futon, pillow and the like of the present invention, the pillow body or principal constituent can easily be separated from its magnets-containing portion, respectively, thus the contents of the futon, pillow or the like other than the magnets-containing portion can easily be exchanged by fresh contents, or re-willowed or regenerated.

What is claimed is:

1. A head-cooling pillow for providing a sound sleep and good health to a sleeper comprising:
    (a) a pillow body;
    (b) a pillow pad including means to detachably mount it to said pillow body;
    (c) said pillow pad including a plurality of parallel envelopes removably contained by an upper and lower cover means;
    (d) a plurality of permanent magnets arranged in spaced relationship on the upper surface of each of said envelopes; and
    (e) a heat-absorptive material disposed in each of said envelopes;
    (f) said heat-absorptive material filling each envelope, whereby said envelopes may easily transform in right and left as well as top and bottom directions.

2. The pillow as claimed in claim 1 wherein said heat-absorptive material is adzuki beans.

3. The pillow as claimed in claim 1 wherein said envelopes are spaced from each other so that said pillow pad transforms easily and fits said pillow body.

4. The pillow as claimed in claim 1 wherein each of said magnets has a surface magnetic flux density of over 500 gauss.

* * * * *

UNITED STATES PATENT OFFICE
CERTIFICATE OF CORRECTION

Patent No. 4,330,892                Dated May 25, 1982

Inventor(s) Kyuji Fukushima

It is certified that error appears in the above-identified patent and that said Letters Patent are hereby corrected as shown below:

Column 1, line 23, "flow" should be --flows--.

Column 1, line 31, "electrically" should be --electricity--.

Column 1, line 63, "to keep" should read --of keeping--.

Column 2, line 33, "transforms" should be --transform--.

Signed and Sealed this

Twenty-fourth Day of August 1982

[SEAL]

Attest:

GERALD J. MOSSINGHOFF

Attesting Officer   Commissioner of Patents and Trademarks